(12) United States Patent
No

(10) Patent No.: US 6,413,554 B1
(45) Date of Patent: Jul. 2, 2002

(54) COMPOSITIONS FOR TREATMENT OF HYPERLIPIDEMIA AND ANGINA PECTORIS

(76) Inventor: Yong Il No, 1414-608 Maehwa Apt., Sanbon-Dong 1015, Gunpo-City, Kyonggi-Do (KR)

( * ) Notice: Subject to any disclaimer, the term of this patent is extended or adjusted under 35 U.S.C. 154(b) by 0 days.

(21) Appl. No.: 09/757,907

(22) Filed: Jan. 10, 2001

(30) Foreign Application Priority Data

Nov. 14, 2000 (KR) .............................................. 00-67315

(51) Int. Cl.$^7$ ................................................ A61K 35/78
(52) U.S. Cl. ....................... 424/739; 424/725; 424/746; 424/754; 424/773; 424/775; 424/776
(58) Field of Search ................................. 424/725, 739, 424/746, 754, 773, 775, 776

(56) References Cited

U.S. PATENT DOCUMENTS 5,958,499 A * 9/1999 Desai et al.

FOREIGN PATENT DOCUMENTS

WO WO/9919365 * 4/1999

OTHER PUBLICATIONS

Sato et al. Sci. Rep. Yokohama Natl. Univ. Sect. ll Biol. Geol. vol. 0 (36), pp. 45–56, BIOSIS abstr. enclosed.*

* cited by examiner

*Primary Examiner*—Christopher R. Tate
(74) *Attorney, Agent, or Firm*—Ladas & Parry

(57) ABSTRACT

The present invention relates to a galenic composition effective for prevention and treatment of hyperlipidemia and ischemia, and angina pectoris due to reperfusion. More specifically, the present invention relates to a composition effective for prevention and treatment of hyperlipidemia and cardiovascular disorders, particularly, angina pectoris due to myocardial ischemia, which contains eight (8) kinds of medicinal herbs consisting of *Allium thumbergii*, trichosanthis semen, angelicae gigantis radix, salviae radix, cinnamomi ramulus, curcumae tuber, paeoniae rubrae radix and pinelliae rhizoma as the major ingredients.

5 Claims, No Drawings

COMPOSITIONS FOR TREATMENT OF HYPERLIPIDEMIA AND ANGINA PECTORIS

FIELD OF THE INVENTION

The present invention relates to a gelenic composition effective for prevention and treatment of hyperlipidemia, and angina pectoris due to ischemia and reperfusion. More specifically, the present invention relates to a galenic composition effective for prevention and treatment of hyperlipidemia and cardiovascular disorders, particularly, angina pectoris due to myocardial ischemia, which contains eight (8) kinds of medicinal herbs consisting of *Allium thumbergii*, trichosanthis semen, angelicae gigantis radix, salviae radix, cinnamomi ramulus, curcumae tuber, paeoniae rubrae radix and pinelliae rhizoma as the major ingredients.

BACKGROUND OF THE INVENTION

In many countries, including Korea, which are under gradual Westernization of dietary life and cultural activities, diseases of adult peoples have been raised as one of serious social problems. Among them, particularly, hyperlipidemia which attacks preferentially the middle forties and has been known as a typical type of diseases developed predominantly in advanced countries has also been raised as one of most common diseases of adult peoples. Hyperlipidemia, which has been known as the main cause of arteriosclerosis and as having a deep correlation with angina pectoris, myocardial infarction and cerebral apoplexy, generally means the blood cholesterol level of 240 mg/dl or more, and it has been proposed that blood cholesterol level should be lowered to the normal value below 200 mg/dl. The major constituents of lipid present in blood are generally classified into total cholesterol, which is commonly called cholesterol, neutral fat (triglyceride), low density lipoprotein, very low density lipoprotein and high density lipoprotein. It has been disclosed that the cause of hyperlipidemia includes heredity, alcohol intake, high fat and high calorie diet, obesity, diabetes, liver functional disorders, thyroid functional disorders and nephritic syndrome.

In general, if hyperlipidemic state is continued, arteriosclerosis may be caused through the pathway that fat plaque is deposited and attached to vascular wall to induce fibrosis and then calcium is deposited thereon. Ultimately, due to such pathway the inside of artery becomes narrower.

As the therapeutic method for treatment of hyperlipidemia, a dietetic treatment has been generally and preferentially selected at present. However, if hyperlipidemic state is not improved by such a dietetic treatment, medicinal drugs such as bile acid-binding resins, nicotinic acid derivatives, pyruvic acid derivatives, probucol, etc. have been used. Recently, HMG CoA reductase inhibitors have been very commonly used as the therapeutic agent for hyperlipidemia. However, any of such medicinal drugs could not provide a satisfactory effect in clinical field as yet.

Cardiovascular system supplies oxygen, nutrients, hormones, etc. necessary for activities of individual organs and tissues and, at the same time, removes waste materials such as carbon dioxide, lactic acid, etc., as produced in respective cells, via blood circulation, thereby allowing the maintenance of normal physiological state in human body. Particularly, heart performs a function as biological circulatory pump by means of its inherent regular contractility to play a decisive role in normal activities of cardiovascular system. Therefore, the abnormality of heart function induces a metabolic disorder of substances present in human body and ultimately, induces a direct disorder of biological phenomenon. Cardiovascular diseases including congestive heart failure, coronary artery disorder, myocardial infarction, hypertension, etc., are a typical disease of adult peoples in modem society and have been raised as a serious social problem since million persons or more in advanced countries annually suffer from such diseases. Particularly, in case of persons managing modem city life, in spite of an increase of interest in prevention and treatment of such cardiovascular diseases, their morbidity is continuously on an increasing trend. Angina pectoris is a kind of cardiagra syndromes originated from transient myocardial ischemia and means a transient cardiagra attack due to coronary insufficiency.

Angina pectoris is a kind of acute coronary insufficiency. Although coronary artery has an ability of sufficiently expanding their lumen, when lumen of blood vessel is narrowed or occluded due to coronary arteriosclerosis, blood flow cannot be increased to the level necessary for cardiac muscle so that cardiac muscle may fall into ischemic state. When such ischemic state of cardiac muscle occurs for a short time, the subjective symptom which may be developed is just angina pectoris. Angina pectoris is characterized by the fact that coronary insufficiency is lasted only for a short period and the unique clinical symptom is only cardiagra attack, and has no objective symptom to make its diagnosis difficult.

At present, when angina pectoris is developed, nitroglycerine is administered via sublingual route. In this case, nitroglycerine is immediately absorbed into mucous membrane to rapidly show its pharmacological activity. Nitro-based agents such as nitroglycerine have a potent activity for dilation of peripheral artery to reduce the preload and postload of heart so that cardiac momentum can be reduced and therefore, the attack of angina pectoris may be lightened and its frequency may also be reduced. Further, nitroglycerine has an activity for dilating collateral circulation of coronary artery to increase the blood flow of coronary artery. However, since nitroglycerine has a little effect on coronary contraction and thus, has a problem that it should be administered together with calcium antagonist.

At present, in order to prevent angina pectoris nitro-based agents are internally administered. However, since such agents do not exhibit sustained activity, recently a sustained release preparation has been used. Further, ointment or tape preparations may also be used so that the active substance can be absorbed into skin. Calcium antagonists have a potent activity of reducing postload of heart and therefore, have also been used as an agent for prevention of angina pectoris. Beta-blocking agents are an agent for reducing cardiac contractility and therefore, can also be used as an agent for prevention of angina pectoris. However, in order to prevent the shift from angina pectoris to myocardial infarction numerous platelet inhibitors should be used, and further if localized stenosis is found by coronary angiography, percutaneous transluminal coronary angioplasty using balloon between aorta and coronary artery, or coronary bypath operation should be practiced. Thus, a satisfactory therapeutic method for angina pectoris has not been developed as yet to impose a heavy economical and time burden on patients.

Thus, the present inventor has assiduously and extensively examined numerous herbal medicines, which have been known as having a little side effect on human body, by combining them in various mixing ratio for a long period, in order to develop a galenic composition useful for treating hyperlipidemia and angina pectoris. As a result, he has found through numerous repeated safety and efficacy tests that a galenic composition having a specific constitution as defined in the following achieves the above-mentioned purpose, and thus completed the present invention.

SUMMARY OF THE INVENTION

The present invention relates to a galenic composition effective for prevention and treatment of hyperlipidemia, and angina pectoris due to ischemia and reperfusion. More specifically, the present invention relates to a galenic composition effective for prevention and treatment of hyperlipidemia and cardiovascular disorders, particularly, angina pectoris due to myocardial ischemia, which contains eight (8) kinds of medicinal herbs consisting of *Allium thumbergii*, trichosanthis semen, angelicae gigantis radix, salviae radix, cinnamomi ramulus, curcumae tuber, paeoniae rubrae radix and pinelliae rhizoma as the major ingredients.

The galenic composition comprising above-mentioned eight kinds of medicinal herbs according to the present invention has been demonstrated by experimental result that it is very effective for prevention and treatment of hyperlipidemia and angina pectoris due to myocardial ischemia by various actions and mechanisms of respective medicinal herbs constituting the composition. Particularly, it has been identified that when the galenic composition of the present invention is repeatedly administered, it shows a superior inhibitory activity against hyperlipidemia and reduces the level of cholesterol and triglyceride in blood. Further, the galenic composition of the present invention inhibits the damage of heart function which may be caused by ischemia and reperfusion, and therefore, provides a very useful effect for prevention and treatment of angina pectoris due to ischemic cardiac muscle.

DETAILED DESCRIPTION OF THE INVENTION

Hereinafter, respective medicinal herbs constituting the galenic composition of the present invention will be specifically explained.

*Allium thumbergii* is a perennial herbal plant which is generally grown in the bush at steep mountain slope and the field. It has been known that *Allium thumbergii* allows to make the body warm and is effective for dyspepsia, neuralgia, brash, etc.

Trichosanthis semen is a seed of *Trichosanthes kirilowii* Maxim belonging to Cucurbitaceae, which is a perennial vinery herbal plant. It has been used as an agent for treatment of diabetes, diuresis, apoplexy, jaundice, tuberculosis, etc.

Angelicae gigantis radix is a root of *Angelica gigas* Nakai belonging to Apiaceae, which has been generally and widely used in the field of Chinese medicine for treating blood-related diseases, gynecologic diseases including dysmenorrhea and menopause, etc.

Salviae radix is a root of *Salvia miltiorrhiza* Bge. belonging to Labiatae, which has been known as having a superior effect on extravasated blood, contusion, neuralgia, arthritis, and particularly, gynecologic diseases and dysmenorrhea.

Cinnamomi ramulus is a bark of *Cinnamomum loureirii* Nees belonging to Lauraceae, which has been used in the field of Chinese medicine for treatment of gastric disorders including diarrhea, vomiting, etc., dysmenorrhea, amenorrhea, menorrhalgia, postpartum abdominal pain. Further, it has also been used for chronic furuncle, incurable skin ulcer, scapula dorsalgia, acroarthralgia, etc.

Curcumae tuber is a subterranean stem of *Curcumae aromatica* Salisb. belonging to Zingiberaceae. It has been widely known that curcumae tuber has a cholagogic effect and an effect of stimulating deintoxication ability of liver.

Paeoniae rubrae radix is a root of *Paeonia lactiflora* Pallas belonging to Paeoniaceae. In the field of Chinese medicine, paeoniae rubrae radix has been used for stypsis, irritable bowel syndrome, spasm of limbs, abdominal pain, spasm, pain, dizziness, tinnitus, hepatitis, anemia, gynecologic diseases, allergy, inflammation, etc.

Pinelliae rhizoma is a subterranean stem of *Pinellia ternate* Breitenbach belonging to Araceae, which has been used in the field of Chinese medicine for providing antitussive and antivomiting effects.

In the composition of the present invention, pharmacological activities peculiar to respective eight medicinal herbs as stated above are harmonized and complemented with each other to exhibit a superior effect for prevention and treatment of hyperlipidemia and angina pectoris, which can never be obtained by using medicinal herbs individually or in a combination of a part thereof.

In the galenic composition according to the present invention, it is preferred to combine respective medicinal herbs in the ratio of *Allium thumbergii* 1–10, trichosanthis semen 0.5–6, angelicae gigantis radix 0.5–6, salviae radix 0.5–6, cinnamomi ramulus 0.1–5, curcumae tuber 0.1–5, paeoniae rubrae radix 0. 1–5 and pinelliae rhizoma 0.1–5, on the basis of dry weight.

More preferably, in the galenic composition according to the present invention respective medicinal herbs can be combined in the ratio of *Allium thumbergii* 3–6, trichosanthis semen 1–4, angelicae gigantis radix 1–4, salviae radix 1–4, cinnamomi ramulus 0.5–3, curcumae tuber 0.5–3, paeoniae rubrae radix 0.5–3 and pinelliae rhizoma 0.5–3, on the basis of dry weight.

In the most preferred galenic composition according to the present invention, respective medicinal herbs can be combined in the ratio of *Allium thumbergii*:trichosanthis semen:angelicae gigantis radix:salviae radix:cinnamomi ramulus curcumae tuber:paeoniae rubrae radix:pinelliae rhizoma=1.5:0.8:0.8:0.8:0.6:0.6:0.6:0.6, on the basis of dry weight. The above defined mixing ratio of medicinal herbs was established through numerous experiments over several years in consideration of the content and efficacy of effective components contained in respective medicinal herbs. Thus, if the mixing ratio of respective medicinal herbs is beyond the above range, the desired pharmacological effect may not be obtained from the galenic composition of the present invention.

Meanwhile, the galenic composition of the present invention can further contain a white liquor as an adjuvant substance so that respective medicinal herbs can sufficiently exhibit their functions and activities. As the white liquor which can be used in the present invention, one or more selected from the group consisting of Kaoliang wine, clear strained rice wine and refined rice wine can be added, if desired. It is preferred to use the white liquor substance in the same amount as water (distilled water) introduced into the extractor to obtain the extract from the galenic composition.

Although the dosage of the galenic composition of the present invention to be administered to the patients can be varied depending on age, sex, healthy condition of the patient, complications, history of surgical operation, administration frequency, etc., when the composition is administered to healthy adult man (body weight 70 kg) three times a day, the daily dosage as calculated on the basis of the extract of the galenic composition obtained from the extractor is suitably in the range of 200–400 cc, which is divided into three doses and administered within 30 minutes to one hour after breakfast, lunch and dinner.

In using the galenic composition of the present invention for clinical purpose, the composition can be formulated according to the conventional method used in the pharmaceutical field into injections, solutions, pills, tablets, capsules, suspensions. etc. In case of oral administration, the composition can be formulated into granules, powders, etc., or can also be filled in a suitable capsule. It can be preferably administered three times a day, in a dose of 5 to 20 g each time, for healthy adult man.

The present invention is more specifically explained by the following examples. However, it will be apparent to a person having an ordinary knowledge in the relevant technical field that these examples are provided only for illustration of the present invention but not intended to limit the scope of the present invention in any manner.

EXAMPLE 1

300 g of *Allium thumbergii,* 160 g of trichosanthis semen, 160 g of angelicae gigantis radix, 160 g of salviae radix, 120 g of *cinnamomi ramulus,* 120 g of curcumae tuber, 120 g of paeoniae rubrae radix and 120 g of pinelliae rhizoma were respectively weighed and ground, and then sequentially introduced into a circulating non-pressurized extractor for Chinese medicine. After adding 1 l of distilled water, the mixture was immersed for one hour and then, 2 l of distilled water and 3 l of refined rice wine were additionally introduced into the extractor. The mixture was extracted with heating at 100° C. for 2.5 hours. The extract was filtered to obtain 3000 cc of the liquid galenic composition of the present invention. 3000 cc of the liquid galenic composition thus obtained was lyophilized to obtain 300 g of the granular composition, which was then pulverized and then used as the test material for the experiment using rats.

EXAMPLE 2

300 g of *Allium thumbergii,* 150 g of trichosanthis semen, 150 g of angelicae gigantis radix, 160 g of salviae radix, 100 g of *cinnamomi ramulus,* 120 g of curcumae tuber, 100 g of paeoniae rubrae radix and 120 g of pinelliae rhizoma were respectively weighed and ground, and then sequentially introduced into a circulating non-pressurized extractor for Chinese medicine. After adding 3 l of distilled water, the mixture was immersed for one hour and then, 3 l of refined rice wine was additionally introduced into the extractor. The mixture was extracted with heating at 100° C. for 3 hours. The extract was filtered to obtain 3000 cc of the liquid galenic composition of the present invention. 3000 cc of the liquid galenic composition thus obtained was lyophilized to obtain 300 g of the granular composition.

In the following experiments, the powdery galenic composition as prepared in Example 1 was used as the test material according to the present invention.

Experiment 1

Toxicity Test for a Single Oral Administration of the Galenic Composition of the Present Invention Using Rats The solid powdery galenic composition of the present invention as prepared in Example 1 was used as the test material. In order to investigate the acute toxicity caused by oral administration of the test material to rats, the test material was orally administered one time to SD (Sprague-Dawley) male rats in two different doses of 2 g/kg and 5 g/kg, wherein five rats were used for respective doses. Then, the mortality, general symptoms, weight change and autopsy findings were observed for 14 days.

1. Test material: Solid powdery galenic composition prepared in Example 1
2. Control medium material: Sterilized distilled water
3. Materials and methods:
    1) Test animal: Specific pathogen-free (SPF) Sprague-Dawley rats
    2) Supplier: Samyouk Experimental Animals Institute
    3) Age and Weight (male)
    Age at a time of receipt: 6 weeks
    Number of animals at a time of receipt: 30 rats
    Weight at a time of receipt: 200–230 g
    Age at a time of start of administration: 7 weeks
    Weight at a time of start of administration: 200–230 g
    4) Quarantine and Adaptation
    At the time of obtaining, the test animals were examined by macrography and then adapted to the animal laboratory in which the test is conducted, for 14 days during which the general signs were observed to select only healthy animals to be used in the experiment.
4. Breeding Environment
    1) Environmental Condition
    This test was practiced in the breeding chamber of Sungkyunkwan University, College of Pharmacy, which was established at temperature of 23±3° C., relative humidity of 50±10%, lightening time of 12 hours (a.m. 8 to p.m. 8) and illumination of 300 to 500 Lux. All the experimenters practiced the test procedures with wearing sterilized working clothes, fatigue caps, masks and gloves.
    2) Breeding Cage, Breeding Density and Discrimination of Breeding Cage During the period for observation after the period for adaptation, quarantine and group dividing, the test animals were introduced into the breeding cage made of polycarbonate (240 W×290 L×175 H mm) with 5 animals for each cage. During the test period, the breeding cages were labeled with the discriminating card in which the test number and the animal number were recorded.
    3) Feeding Method
    The solid feed for rodents was purchased from Jell Trading Company and observed by macrography whether it is contaminated with foreign materials or not, before using in the experiment. In this test, all the test animals were allowed to freely intake the powdery feed. Further, animals were also allowed to freely drink tap water.
5. Dosage and Constitution of Test Groups
    1) Dosage
    On the basis of the result obtained from preliminary experiments for test dosage of the galenic composition according to the present invention, the maximum dosage, which can be administered to rats was determined to be 5 g per kg of rat, which was dissolved in sterilized distilled water and used as the highest dosage. Two dosage groups were established which are composed of 2 g/kg dosage group and the highest dosage group.
    2) Constitution of Test Groups, Dosage and Amount

| Test groups | | Number of animals | Amount of solution (mg/kg) | Dosage (g/kg) |
|---|---|---|---|---|
| Control group | sterilized | 5 | 10 | |

-continued

| Test groups | distilled water | Number of animals | Amount of solution (mg/kg) | Dosage (g/kg) |
|---|---|---|---|---|
| Test material | present invention | 5 | 10 | 2 g/kg |
| | | 2 | 10 | 5 g/kg |

3) Group Dividing

The test animals were divided as follows. First, the animals, which were determined as being healthy during adaptation period, were weighed and then the animals close to the average weight were selected and randomly divided into the test groups.

6. Administration of the Test Material

1) Test Material

The solid powdery galenic composition obtained in Example 1 was used as the test material and, on the day of test, was weighed in an amount of 5 g/10 ml/kg and 2 g/10 ml/kg, which were dissolved in sterilized distilled water and used in the test.

2) Administration Route and Method

The test material was forcibly administered to rats, which were allowed to fast for 18 hours before administration, via oral route by means of a syringe provided with sonde for oral administration.

3) Reason for Selection of Administration Route

The oral administration was selected because it is a route for clinical application.

4) Administration Frequency and Duration

In the morning of the day of administration, the test material was single administered for individual subject.

5) Calculation of the Dosing Amount of the Solution to be Administered

The dosing amount of the solution was calculated in terms of 10 ml/kg on the basis of weight on the day of administration.

7. Observation and Examination Items

1) Observation of General Signs and Dead Animals

All the test animals were observed on any change in general signs, toxic symptoms and dead and/or survived animals every hours for 1–6 hours after administration on that day and then, once a day for 14 days from the day following administration.

2) Measuring the Body Weight

All the test animals were weighed immediately before administration of the test material and on the days 3, 7, 10 and 14 after administration.

3) Observation of Autopsy Findings

All the animals survived on the day 14 from administration were anesthetized with ether and then subjected to autopsy to carefully observe any abnormality of appearance and internal organs by macrography examination.

8. Statistical Analysis

The data, including weight, as obtained in this test were statistically analyzed using Student's t-test to examine a significance between the control groups and respective test groups.

9. Test Results

1) Dead Animals and Clinical Symptoms

No dead animal was observed throughout the overall period of test in all the test groups receiving the galenic composition of the present invention (see Table 1 below). Further, any particular change in general signs was also not specifically observed in the test groups in comparison to the control group (see Table 2 below).

TABLE 1

Test for acute oral toxicity in rats

| | Dosage (g/kg) | Mortality | Number of deaths Days after dosing | | | | | | | | | | | | | |
|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 |
| Control group | | 0/5 | 0 | 0 | 0 | 0 | 0 | 0 | 0 | 0 | 0 | 0 | 0 | 0 | 0 | 0 |
| Test group (galenic composition) | 2 | 0/5 | 0 | 0 | 0 | 0 | 0 | 0 | 0 | 0 | 0 | 0 | 0 | 0 | 0 | 0 |
| | 5 | 0/5 | 0 | 0 | 0 | 0 | 0 | 0 | 0 | 0 | 0 | 0 | 0 | 0 | 0 | 0 |

TABLE 2

Change in general signs in rats orally treated with the galenic composition of the present invention

| | Dosage (g/kg) | Days after dosing | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| Control group | | —* | — | — | — | — | — | — | — | — | — | — | — | — | — |
| Test group (galenic composition) | 2 | — | — | — | — | — | — | — | — | — | — | — | — | — | — |
| | 5 | — | — | — | — | — | — | — | — | — | — | — | — | — | — |

Note)
*No abnormality detected.

2) Measuring the Body Weight

A change in body weights of rats in all the test groups receiving the galenic composition of the present invention is not significantly different from that of the control group (see Table 3 below).

TABLE 3

Change in body weight of rats orally treated with the galenic composition of the present invention

| Dose (g/kg) | No. of animal | Body weight (g) Days after dosing | | | | |
|---|---|---|---|---|---|---|
| | | 1 | 3 | 7 | 10 | 14 |
| Control group | | | | | | |
| | 1 | 210 | 250 | 260 | 270 | 260 |
| | 2 | 210 | 250 | 270 | 280 | 250 |
| | 3 | 230 | 260 | 270 | 280 | 250 |
| | 4 | 220 | 260 | 260 | 280 | 280 |
| | 5 | 210 | 230 | 200 | 180 | 180 |
| | Result | 216 ± 9 | 250 ± 12 | 252 ± 29 | 258 ± 44 | 244 ± 38 |
| Test group (galenic composition) | | | | | | |
| 2 | 1 | 210 | 230 | 240 | 230 | 200 |
| | 2 | 220 | 240 | 240 | 240 | 220 |
| | 3 | 200 | 240 | 210 | 230 | 200 |
| | 4 | 230 | 250 | 240 | 240 | 220 |
| | 5 | 210 | 240 | 230 | 200 | 190 |
| | Result | 214 ± 11 | 240 ± 7 | 232 ± 13 | 228 ± 16 | 206 ± 13 |
| Test group (galenic composition) | | | | | | |
| 5 | 1 | 210 | 250 | 260 | 240 | 200 |
| | 2 | 210 | 240 | 250 | 250 | 220 |
| | 3 | 230 | 260 | 270 | 280 | 240 |
| | 4 | 230 | 250 | 260 | 240 | 210 |
| | 5 | 210 | 240 | 250 | 250 | 220 |
| | Result | 218 ± 11 | 248 ± 8 | 258 ± 8 | 252 ± 16 | 218 ± 15 |

In the numerical values were recorded in terms of mean±standard deviation (S.D.) and the number of rats used in each group was 5.

3) Macrographic Anatomical Findings

Any abnormal finding was not found by observing the organs of rats receiving the galenic composition of the present invention (see Table 4 below).

TABLE 4

Any abnormality in the organs of rats orally treated with the galenic composition of the present invention

| Dose (g/kg) | No. of animal | Observation Days after dosing | | | | |
|---|---|---|---|---|---|---|
| | | 1 | 3 | 7 | 10 | 14 |
| Control group | | | | | | |
| | 1 | N.G.L.[a] | N.G.L. | N.G.L. | N.G.L. | N.G.L. |
| | 2 | N.G.L. | N.G.L. | N.G.L. | N.G.L. | N.G.L. |
| | 3 | N.G.L. | N.G.L | N.G.L. | N.G.L. | N.G.L. |
| | 4 | N.G.L. | N.G.L. | N.G.L. | N.G.L. | N.G.L. |
| | 5 | N.G.L. | N.G.L. | N.G.L. | N.G.L. | N.G.L. |
| Test group (galenic composition) | | | | | | |
| 2 | 1 | N.G.L. | N.G.L. | N.G.L. | N.G.L. | N.G.L. |
| | 2 | N.G.L. | N.G.L. | N.G.L. | N.G.L. | N.G.L. |
| | 3 | N.G.L. | N.G.L. | N.G.L. | N.G.L. | N.G.L. |
| | 4 | N.G.L. | N.G.L. | N.G.L. | N.G.L. | N.G.L. |
| | 5 | N.G.L. | N.G.L. | N.G.L. | N.G.L. | N.G.L. |
| Test group (galenic composition) | | | | | | |
| 5 | 1 | N.G.L. | N.G.L. | N.G.L. | N.G.L. | N.G.L. |
| | 2 | N.G.L. | N.G.L. | N.G.L. | N.G.L. | N.G.L. |
| | 3 | N.G.L. | N.G.L. | N.G.L. | N.G.L. | N.G.L. |
| | 4 | N.G.L. | N.G.L. | N.G.L. | N.G.L. | N.G.L. |
| | 5 | N.G.L. | N.G.L. | N.G.L. | N.G.L. | N.G.L. |

TABLE 4-continued

Any abnormality in the organs of rats orally treated with the galenic composition of the present invention

| Dose (g/kg) | No. of animal | Observation Days after dosing | | | | |
|---|---|---|---|---|---|---|
| | | 1 | 3 | 7 | 10 | 14 |

Note)
[a]No gross lesions

10. Conclusion

As shown in the above Tables 1 to 4, as the result of the toxicity test practiced by single administering the galenic composition of the present invention via oral route both of the control group and the test groups exhibited neither dead animals and clinical symptoms nor abnormal signs in anatomical findings. Thus, it could be identified that the galenic composition of the present invention as used in this test does not show any toxicity even at a dosage up to 5 g/kg. Therefore, it is concluded that NOASEL (no observed adverse effect level) of the galenic composition of the present invention in rats is 5 g/kg or more.

Experiment 2

Test for the Effect of the Galenic Composition of the Present Invention on Hyperlipidemia (Single and Repeated Administration)

In order to evaluate the pharmacological effect of the galenic composition of the present invention, which comprises the combined extract of medicinal herbs and is supposed to have a superior effect on hyperlipidemia, the effect of the galenic composition of the present invention by single and repeated administration was determined in rats suffering from hyperlipidemia induced by tyloxapol (Triton WR-1339, isooctylpolyoxyethylene phenol). The galenic composition of the present invention was orally administered to hyperlipidemic rats, which were allowed to fast for 18 hours before test, in respective dosages (single administration test: 500, 1000, 1500 mg/kg, repeated administration test: 300, 600, 900 mg/kg) once or for 7 days. Tyloxapol as an agent for inducing hyperlipidemia was injected into tail vein in an amount of 1 ml/kg.

Then, the contents of triglyceride and total cholesterol in serum were measured. Further, in some test groups the contents of high density lipoprotein (HDL) and low density lipoprotein (LDL) were also measured. As a result, the galenic composition of the present invention did not show an effect of inhibiting tyloxapol-induced hyperlipidemia by a single administration but exhibited a superior effect of inhibiting tyloxapol-induced hyperlididemia by repeated administration in the 600 and 900 mg/kg test groups. Therefore, it could be identified that the repeated administration of the galenic composition according to the present invention exhibits a superior effect of inhibiting tyloxapol-induced hyperlipidemia. From this result, it is considered that the galenic composition of the present invention has an activity for inhibiting synthesis of, and for stimulating excretion of, cholesterol increased by tyloxapol treatment.

1. Test Materials and Test Method

1) Test Animals

SD line male rats weighing about 220 g were obtained from Jell Trading Company, adapted for one week or more in the animal breeding chamber of the present laboratory in which the humidity was maintained at a constant level, and then observed for general conditions to screen the healthy animals in appearance, which were used in the experiment, All the test animals were allowed to fast for 18 hours befre induction of hyperlipidemia, but to freely intake water.

2) Test Materials

The powdery galenic composition prepared in Example 1 was used as the test material and tyloxapol (isooctylpolyoxyethylene phenol, Triton WR 1339) used as an agent for inducing hyperlipidemia was purchased from Sigma-Aldrich. Triglyceride and total cholesterol levels in serum were measured by means of a kit purchased from Asan Pharm. Co., Ltd., and other reagents were the first-grade reagents sold in Korea.

3) Preparation of the Test Material

The powdery galenic composition obtained in Example 1 was used as the test material. The galenic compositions corresponding to respective test dosages and tyloxapol in an amount of 200 mg/kg were dissolved in sterilized distilled water in order to use in the experiment.

Test group—The groups of test animals were divided as follows:

Single Administration Test
    a. Control group (sterilized distilled water)
    b. Group treated only with tyloxapol (200 mg/kg)
    c. Galenic composition (500 mg/kg)+Tyloxapol (200 mg/kg)
    d. Galenic composition (1000 mg/kg)+Tyloxapol (200 mg/kg)
    e. Galenic composition (1500 mg/kg)+Tyloxapol (200 mg/kg)

Repeated Administration Test
    a. Control group (sterilized distilled water)
    b. Group treated only with tyloxapol (200 mg/kg)
    c. Galenic composition (300 mg/kg)+Tyloxapol (200 mg/kg)
    d. Galenic composition (600 mg/kg)+Tyloxapol (200 mg/kg)
    e. Galenic composition (900 mg/kg)+Tyloxapol (200 mg/kg)

4) Test Method

Single Administration Method

The galenic compositions corresponding to respective dosages (500, 1000, 1500 mg/kg) were orally administered in the volume of 10 ml/kg to the test animals, which were allowed to fast for 18 hours, and on the day of 7 tyloxapol was administered immediately after which the test animals were anesthetized with ether and blood was collected. Tyloxapol was injected into tail vein in the volume of 1 ml/kg.

Repeated Administration Method

The galenic compositions corresponding to respective dosages (300, 600, 900 mg/kg) were orally administered for 6 days once a day in the volume of 10 ml/kg to the test animals, which were allowed to fast for 18 hours, and on the day of 7 tyloxapol was administered immediately after which the test animals were anesthetized with ether and blood was collected. Tyloxapol was injected into tail vein in an amount of 1 ml/kg.

5) Blood collecting method: Blood was collected from eyeball of the test animals in an amount of about 1 ml before and 6, 24 and 48 hours after administration of tyloxapol. The collected blood was centrifuged for 2 minutes at 10000 rpm by means of a centrifuge to separate serum only, which was then used for analysis.

6) Blood analysis: The contents of triglyceride and total cholesterol in serum were measured by means of a kit purchased from Asan Pharm. Co., Ltd.. The contents of high density lipoprotein (HDL) and low density lipoprotein (LDL) were measured only in the test groups for repeated administration on 6 and 24 hours at Handok Clinical Pathology Center.

2. Statistical Analysis

The statistical significance for respective test groups was examined in the following manner. The data obtained in respective test groups were subjected to Levene's test to identify their variance homogenicity. When the variance is homogeneous, the data were subjected to one-way ANOVA and then, if the significance is recognized at the level of p=0.05, the difference between respective test groups was compared by Dunnett t test (Procedure A). When the variance is heterogeneous, the data transformation was practiced and the transformed data were subjected again to Levene's test. Then, if the variance is homogeneous, the data were examined according to Procedure A. However, if the variance is heterogeneous, the data were subjected to non-parametric ANOVA test. Then, if the result of non-parametric ANOVA test is significant, the statistical significance of the data was examined according to Wilcoxon-Mann-Whitney rank sum test or Nemenyi-Kruskal-Wallis multiple comparisons test (Procedure B).

3. Experimental Result

1) Effect of the Single Administration of the Galenic Composition on Blood Triglyceride Content The results obtained from the test for observing a change in serum triglyceride content by single administration of the galenic composition of the present invention to hyperlipidemia are shown in Table 5. The control group showed a substantially uniform content of triglyceride as the values of 86.0 to 126.3 mg/dl throughout the overall experimental period, and all the test groups also showed uniform levels as 87.6 to 101.2 mg/dl before administration of tyloxapol. However, in the test group treated only with tyloxapol the triglyceride content was increased to 1878.1 and 1275.1 mg/dl after 6 and 24 hours from administration, respectively, which are 23 and 11 times or more, respectively, the level in the control group at the same time period, and then was recovered to the normal level (102.0 mg/dl) after 48 hours. However, a sharp increase in triglyceirde content after 6 and 24 hours from tyloxapol treatment was not inhibited by single administration of the galenic composition of the present invention at all the dosing levels (500, 1000, 1500 mg/kg).

TABLE 5

Effect of the single administration of the galenic composition on blood triglyceride content in rats

| Test group | Dosage (mg/kg) | Triglyceride (mg/dl) | | | |
|---|---|---|---|---|---|
| | | Before dosing | After 6 hr. | After 24 hr. | After 48 hr. |
| Control group | 0 | 86.0 ± 39.4 | 81.1 ± 19.9 | 109.1 ± 23.3 | 126.3 ± 42.9 |
| Tyloxapol | 200 | 77.4 ± 18.6 | 1878.1 ± 256.8*** | 1275.1 ± 668.7*** | 102.0 ± 25.3 |
| Galenic + Tyloxapol | 500 200 | 87.6 ± 24.9 | 1895.8 ± 200.3*** | 1348.7 ± 439.5*** | 122.2 ± 30.9 |
| Galenic + Tyloxapol | 1000 200 | 97.7 ± 25.3 | 1906.4 ± 98.4*** | 1238.8 ± 654.8*** | 125.5 ± 41.8 |
| Galenic + Tyloxapol | 1500 200 | 101.2 ± 30.2 | 1837.6 ± 311.0*** | 1353.3 ± 523.9*** | 125.2 ± 58.7 |

Note)*** : Significantly different from the control group in 99.9% confidence interval ($p < 0.001$)

In the above table, the numerical values were recorded in terms of mean ± standard deviation (S.D.) and the number of rats used in each test group was 9 to 10.

2) Effect of the Single Administration of the Galenic Composition on Total Cholesterol Content in Blood The results obtained from the test for observing a change in blood total cholesterol content by single administration of the galenic composition of the present invention to hyperlipidemia are shown in Table 6. As in the case of triglyceride content, the control group showed a substantially uniform content of total cholesterol as the values of 54.3 to 65.2 mg/dl throughout the overall experimental period, and all the test groups also showed uniform levels as 49.1 to 56.0 mg/dl before administration of tyloxapol. However, in the test group treated only with tyloxapol the total cholesterol content was significantly increased to 190.2 and 272.8 mg/dl after 6 and 24 hours from administration, respectively, which are 3 times or more the level in the control group at the same time period, and then was recovered to the normal level (71.1 mg/dl) after 48 hours. However, an increase in blood total cholesterol level after 6 and 24 hours from tyloxapol treatment was not inhibited by single administration of the galenic composition of the present invention.

TABLE 6

Effect of the single administration of the galenic composition on blood total cholesterol content in rats

| Test group | Dosage (mg/kg) | Total cholesterol (mg/dl) | | | |
|---|---|---|---|---|---|
| | | Before dosing | After 6 hr. | After 24 hr. | After 48 hr. |
| Control group | 0 11.0 | 54.3 ± 9.7 9.3 | 67.9 ± | 67.4 ± | 65.2 ± 9.3 |
| Tyloxapol | 200 | 49.4 ± 8.1 | 190.2 ± 19.3*** | 272.8 ± 60.9*** | 71.1 ± 11.5 |

TABLE 6-continued

Effect of the single administration of the galenic composition on blood total cholesterol content in rats

| Test group | Dosage (mg/kg) | Total cholesterol (mg/dl) | | | |
|---|---|---|---|---|---|
| | | Before dosing | After 6 hr. | After 24 hr. | After 48 hr. |
| Galenic + Tyloxapol | 500 200 | 49.1 ± 9.6 12.4*** | 193.6 ± 39.1*** | 255.3 ± | 71.9 ± 6.3 |
| Galenic + Tyloxapol | 1000 200 | 56.0 ± 8.3 15.5*** | 192.7 ± 65.6*** | 246.2 ± | 75.8 ± 9.6* |
| Galenic + Tyloxapol | 1500 200 | 52.8 ± 9.3 16.0*** | 197.0 ± 57.1*** | 274.3 ± | 82.3 ± 8.6*# |

Note) *,***Significantly different from the control group in 95% ($p < 0.05$) and 99.9% ($p < 0.001$) confidence interval
Significantly different from the group treated only with Tyloxapol in 95% confidence interval ($p < 0.05$)

In the above table, the numerical values were recorded in terms of mean ± standard deviation (S.D.) and the number of rats used in each test group was 9 to 10.

3) Effect of the Repeated Administration of the Galenic Composition on Blood Triglyceride Content The results obtained from the test for observing a change in serum triglyceride content by repeated administration of the galenic composition of the present invention to hyperlipidemia are shown in Table 7. The control group showed a substantially uniform content of triglyceride as the values of 90.0 to 143.5 mg/dl throughout the overall experimental period, and all the test groups also showed uniform levels as 67.7 to 79.9 mg/dl before administration of tyloxapol. However, in the test group treated only with tyloxapol the triglyceride content was significantly increased to 1436.7 and 1246.7 mg/dl after 6 and 24 hours from administration, respectively, which are 12 and 8 times or more, respectively, the level in the control group at the same time period, and then was recovered to the normal level (119.0 mg/dl) after 48 hours. However, in the test group repeatedly treated with the galenic composition at the dosage of 300, 600 and 900 mg/kg for 7 days, the 300 mg/kg group could not inhibit an increase in triglyceirde content due to tyloxapol treatment, but the 600 mg/kg group reduced the triglyceride level to 893.8 mg/dl after 24 hours from tyloxapol treatment and the 900 mg/kg group exhibited a significant effect of inhibiting triglyceride level to 436.1 mg/dl after 24 hours, in comparison to the group treated only with tyloxapol. After 48 hours from tyloxapol treatment, all the groups treated with the galenic composition of the present invention recovered blood triglyceride content to the normal level.

TABLE 7

Effect of the repeated administration of the galenic composition on blood triglyceride content in rats

| Test group (No. of animals) | Dosage (mg/kg) | Triglyceride (mg/dl) | | | |
|---|---|---|---|---|---|
| | | Before dosing | After 6 hr. | After 24 hr. | After 48 hr. |
| Control group (7) | 0 | 90.0 ± 51.4 | 117.0 ± 70.3 | 143.5 ± 75.0 | 105.3 ± 39.9 |
| Tyloxapol (9) | 200 | 82.5 ± 31.9 | 1436.7 ± 133.9*** | 1246.7 ± 392.0** | 119.0 ± 41.4 |
| Galenic + Tyloxapol (10) | 300 200 | 79.9 ± 17.9 | 1579.1 ± 262.3*** | 1081.0 ± 706.5* | 115.4 ± 31.2 |
| Galenic + Tyloxapol | 600 200 | 67.7 ± 12.8 | 1475.1 ± 146.48*** | 893.8 ± 420.3 | 102.4 ± 43.4 |

TABLE 7-continued

Effect of the repeated administration of the galenic composition on blood triglyceride content in rats

| Test group | | Triglyceride (mg/dl) | | | |
|---|---|---|---|---|---|
| (No. of animals) | Dosage (mg/kg) | Before dosing | After 6 hr. | After 24 hr. | After 48 hr. |
| (9) Galenic + Tyloxapol (9) | 900 200 | 73.2 ± 17.9 | 1552.4 ± 188.78*** | 436.1 ± 229.8## | 85.8 ± 29.2 |

Note) *,,*Significantly different from the control group in 95%, 99% and 99.9% confidence interval
Significantly different from the group treated only with Tyloxapol in 99% confidence interval In the above table, the numerical values were recorded in terms of mean ± standard deviation (S.D.) and the number of rats used in each test group was 7 to 10.

4) Effect of the Repeated Administration of the Galenic Composition on Total Cholesterol Content in Blood The results obtained from the test for observing a change in blood total cholesterol content by repeated administration of the galenic composition of the present invention to hyperlipidemia are shown in Table 8. The control group showed a substantially uniform content of total cholesterol as the values of 47.2 to 63.8 mg/dl throughout the overall experimental period, and all the test groups also showed uniform levels as 64.9 to 71.0 mg/dl before administration of tyloxapol. However, in the test group treated only with tyloxapol the total cholesterol content was significantly increased to 149.3 and 261.4 mg/dl after 6 and 24 hours from administration, respectively, which are 3 times or more the level in the control group at the same time period (47.2 and 51.5 mg/dl), and after 48 hours, was also a significantly increased level (86.1 mg/dl). However, in the test group repeatedly treated with the galenic composition at the dosage of 300, 600 and 900 mg/kg for 7 days, the 300 mg/kg group could not inhibit an increase in total cholesterol content due to tyloxapol treatment and the 600 mg/kg group reduced the total cholesterol level to 201.5 mg/dl after 24 hours from tyloxapol treatment without any statistical significance. Contrary to this, the 900 mg/kg group exhibited a significant effect of inhibiting total cholesterol level to 150.0 mg/dl after 24 hours, in comparison to the group treated only with tyloxapol. After 48 hours from tyloxapol treatment, all the groups treated with the galenic composition of the present invention showed a significant increase in total cholesterol levels (81.2, 83.1 and 81.7 mg/dl) but exhibited a gradual recovering of blood total cholesterol to the normal level.

TABLE 8

Effect of the repeated administration of the galenic composition on blood total cholesterol content in rats

| Test group | | Total cholesterol (mg/dl) | | | |
|---|---|---|---|---|---|
| (No. of animals) | Dosage (mg/kg) | Before dosing | After 6 hr. | After 24 hr. | After 48 hr. |
| Control group (7) | 0 | 59.9 ± 8.8 | 47.2 ± 6.2 | 51.5 ± 7.4 | 63.8 ± 9.8 |
| Tyloxapol (9) | 200 | 67.3 ± 8.6 | 149.3 ± 64.1*** | 261.4 ± 14.2** | 86.1 ± 16.2*** |
| Galenic + Tyloxapol | 300 200 | 64.9 ± 11.9 | 145.5 ± 9.6*** | 217.7 ± 72.5*** | 81.2 ± 14.2* |
| Galenic + Tyloxapol (9) | 600 200 | 71.0 ± 8.5 | 145.1 ± 16.7*** | 201.5 ± 55.5*** | 83.1 ± 12.1* |
| Galenic + Tyloxapol (9) | 900 200 | 70.7 ± 14.6 | 141.4 ± 11.9*** | 150.0 ± 36.2***## | 81.7 ± 12.7* |

Note) *,,*Significantly different from the control group in 95%, 99% and 99.9% confidence interval
Significantly different from the group treated only with Tyloxapol in 99% confidence interval In the above table, the numerical values were recorded in terms of mean±standard deviation (S.D.) and the number of rats used in each test group was 7 to 10.

5) Effect of the Repeated Administration of the Galenic Composition on LDL Cholesterol Content in Blood The results obtained from the test for observing a change in blood LDL cholesterol content by repeated administration of the galenic composition of the present invention to hyperlipidemia, after 6 and 24 hours from tyloxapol treatment, at which blood total cholesterol level was greatly varied as shown above, are shown in Table 9. The LDL cholesterol level after 6 and 24 hours was 16.1 and 12.3 mg/dl, respectively, in the control group but was significantly increased to 29.0 and 41.6 mg/dl, respectively, in the test groups treated only with tyloxapol. Contrary to this, the test groups repeatedly treated with the galenic composition at the dosage of 300, 600 and 900 mg/kg for 7 days exhibited a tendency to reduce LDL cholesterol level to 22.4 mg/dl in the 300 mg/kg group, 17.0 mg/dl in the 600 mg/kg group, and 19.7 mg/dl in the 900 mg/kg group, after 6 hours from tyloxapol treatment. However, only the 600 mg/kg group exhibited a significant inhibition in comparison to the group treated only with tyloxapol. After 24 hours from tyloxapol treatment, all the test groups treated with the galenic composition at three kinds of dosages exhibited a significant effect of inhibiting LDL level (to 21.5, 15.3 and 19.8 mg/dl, respectively) in comparison to the group treated only with tyloxapol.

TABLE 9

Effect of the repeated administration of the galenic composition on blood LDL Cholesterol level in rats

| Test group | Dosage | LDL cholesterol (mg/dl) | |
|---|---|---|---|
| (No. of animals) | (mg/kg) | After 6 hr. | After 24 hr. |
| Control group (7) | 0 | 16.1 ± 3.6 | 12.3 ± 2.4 |
| Tyloxapol (9, 7) | 200 | 29.0 ± 14.4* | 41.6 ± 12.2*** |
| Galenic + Tyloxapol (9, 10) | 300 200 | 22.4 ± 8.6 | 21.5 ± 8.0**## |
| Galenic + Tyloxapol (9, 8) | 600 200 | 17.0 ± 3.3# | 15.3 ± 3.5### |
| Galenic + Tyloxapol (9) | 900 200 | 19.7 ± 6.2 | 19.8 ± 6.1*### |

Note) *,,*Significantly different from the control group in 95%, 99% and 99.9% confidence interval
, ##, ###Significantly different from the group treated only with Tyloxapol in 95%, 99% and 99.9% confidence interval In the above table, the numerical values were recorded in terms of mean ±standard deviation (S.D.) and the number of rats used in each test group was 7 to 10.

6) Effect of the Repeated Administration of the Galenic Composition on HDL Cholesterol Content in Blood The results obtained from the test for observing a change in blood HDL cholesterol content by repeated administration of the galenic composition of the present invention to hyperlipidemia, after 6 and 24 hours from tyloxapol administration, at which blood total cholesterol level was greatly varied as shown above, are shown in Table 10. The HDL cholesterol level after 6 and 24 hours was 23.0 and 30.3 mg/dl, respectively, in the control group but was increased to 36.2 and 34.3 mg/dl, respectively, in the test groups treated only with tyloxapol with significance only after 6 hours. All the test groups repeatedly treated with the galenic composition at the dosage of 300, 600 and 900 mg/kg for 7 days exhibited a significant increase in HDL cholesterol level to 35.8 mg/dl in the 300 mg/kg group, 35.4 mg/dl in the 600 mg/kg group and 30.6 mg/dl in the 900 mg/kg group, after 6 hours from tyloxapol treatment. After 24 hours from tyloxapol treatment, all the test groups treated with the galenic composition at three kinds of dosages (34.2, 28.6 and 25.6 mg/dl, respectively) exhibited an insignificant difference from the control group.

TABLE 10

Effect of the repeated administration of the galenic composition on blood HDL cholesterol level in rats

| Test group (No. of animals) | Dosage (mg/kg) | HDL cholesterol (mg/dl) | |
|---|---|---|---|
| | | After 6 hr. | After 24 hr. |
| Control group (7) | 0 | 23.0 ± 5.0 | 30.3 ± 3.6 |
| Tyloxapol (9) | 200 | 36.2 ± 4.4*** | 34.3 ± 8.7 |
| Galenic + Tyloxapol (10) | 300 200 | 35.8 ± 7.6*** | 34.2 ± 11.2 |
| Galenic + Tyloxapol (9) | 600 200 | 35.4 ± 5.0*** | 28.6 ± 6.5 |
| Galenic + Tyloxapol (9, 8) | 900 200 | 30.6 ± 3.5* | 25.6 ± 4.1 |

Note) *,*** Significantly different from the control group in 95% ##0.05) and 99.9% (p < 0.001) confidence interval In the above table, the numerical values were recorded in terms of mean±standard deviation (S.D.) and the number of rats used in each test group was 7 to 10.

5. Conclusion

As a result of the test for evaluating the effect of the galenic composition of the present invention comprising the mixed extract of medicinal herbs, which were expected to have a good effect on hyperlipidemia in clinical field, on tyloxapol-induced hyperlipidemia, it could be identified that the single administration of the galenic composition of the present invention at a maximum dosage of 1.5 g/kg has no inhibitory effect on tyloxapol-induced hyperlipidemia. However, in the test for the repeated administration of the galenic composition of the present invention at three kinds of dosages for 7 days, the 600 and 900 mg/kg dosing groups exhibited an effect of inhibiting tyloxapol-induced hyperlipidemia. In general, it has been known that after administration of tyloxapol the hyperlipidemic level reached a maximum value after 24 hours (first stage) and then is reduced to the normal value after 48 hours (second stage), through tyloxapol's mechanism to stimulate the synthesis of cholesterol and to inhibit the excretion and decomposition of lipoprotein in blood. Therefore, if any drug exhibits its effect at the first stage, it is determined to be concerned in the biosynthesis of cholesterol, and if a drug exhibits its effect at the second stage, the drug is determined to be concerned in the excretion and decomposition of cholesterol.

Thus, in view of the fact that the galenic composition of the present invention exhibits a good inhibitory effect after 24 hours and its effect is lasted even after 48 hours, it is considered that the galenic composition of the present invention has an activity for inhibiting synthesis of, and stimulating excretion of, cholesterol increased by tyloxapol treatment.

From the above experimental results, it can be determined that the galenic composition of the present invention as repeatedly administered has an effect of inhibiting hyperlipidemia and inhibits cholesterol biosynthesis and stimulates cholesterol excretion. Further, is can also be determined that the galenic composition of the present invention has no particular effect on high density lipoprotein but has an effect of reducing the contents of low density lipoprotein, total cholesterol and triglyceride in blood. It is preferred that in case of repeated administration the effective dose of the galenic composition is 600 mg/kg or more.

Experiment 3

Test for the Effect of the Galenic Composition of the Present Invention on Cardiac Ischemia and Reperfusion (Single and Repeated Administration)

In order to estimate the pharmacological effect of the galenic composition of the present invention, which comprises the combined extract of medicinal herbs and is considered as having a superior effect on angina pectoris in the clinical field, the effect of the galenic composition of the present invention by single and repeated administration was determined in hearts extracted from rats suffering from ischemia and reperfusion. The galenic composition of the present invention was orally administered to rats fasted for 18 hours before test, at respective dosages (single administration test: 1000, 1500 mg/kg, repeated administration test: 600, 900 mg/kg) once or for 7 days. As a result, the galenic composition of the present invention inhibited the damage of heart function due to ischemia and reperfusion by a single administration of 1000 mg/kg but had no particular effect on the damage of heart function due to ischemia and reperfusion by a single administration of 1500 mg/kg. In the repeated administration test, the damage of heart function due to ischemia and reperfusion was significantly inhibited at a dosage of 600 mg/kg and somewhat inhibited at a dosage of 900 mg/kg. Therefore, it could be identified that the single and repeated administration of the galenic composition according to the present invention exhibits an effect of treating and preventing angina pectoris by inhibiting and preventing the damage of heart function due to ischemia and reperfusion.

1. Test Materials and Test Method

1) Test Animals

SD line male rats weighing about 300 g were obtained from Jell Trading Company, adapted for one week or more in the animal breeding chamber of the present laboratory in which the humidity was maintained at a constant level, and then observed for general conditions to screen the healthy animals in appearance, which were used in the experiment. All the test animals were allowed to fast for 18 hours before test, but to freely intake water.

2) Test Materials

The powdery galenic composition prepared in Example 1 was used as the test material and pyruvate contained in Krebs-Henseleit bicarbonate buffer was purchased from Sigma-Aldrich (Cat. No. P2256). Other reagents were the first-grade reagents sold in Korea.

3) Preparation of the Test Material

The powdery galenic composition obtained in Example 1 was used as the test material. The galenic compositions corresponding to respective test dosages were dissolved in sterilized distilled water in order to use in the experiment.

Test group—The groups of test animals were divided as follows:

Single Administration Test
 a. Control group (sterilized distilled water)
 b. Galenic composition (1000 mg/kg)
 c. Galenic composition (1500 mg/kg)
Repeated Administration Test
 a. Control group (sterilized distilled water)
 b. Galenic composition (600 mg/kg)
 c. Galenic composition (900 mg/kg)
4) Test Method
Single Administration Method The test animals fasted for 18 hours were given the galenic compositions corresponding to respective dosages (1000, 1500 mg/kg) in the volume of 10 ml/kg via oral route, and after 2 hours, used in the experiment.

Repeated Administration Method

The test animals fasted for 18 hours were given the galenic compositions corresponding to respective dosages (600, 900 mg/kg) for 6 days once a day in the volume of 10 ml/kg via oral route, and after 2 hours, used in the experiment.

Heart Extraction and Perfusion in Rats

Rats were anesthetized with sodium pentobarbital (40 mg/kg, i.p.) and then cannulated into femoral artery. Sodium heparin (1000 U/kg, i.v.) was administered via cannula and arterial cannula was in situ inserted into artery in Grover buffer. Then, heart was extracted under retrograde perfusion and immediately suspended in Langendorff apparatus, and after removing unnecessary tissues attached to heart, perfused with Krebs-Henseleit bicarbonate buffer (KHBB) solution (37° C., pH 7.4) saturated with oxygen under perfusion at a constant pressure (55 mmHg). Stainless steel cannula hanging latex balloon filled with distilled water was inserted into left ventricle via pulmonary vein and connected to a pressure transducer (Grass, U.S.A.) to isovolumetrically measure left ventricular pressure transmitted to balloon. After heart is stabilized, LVEDP (left ventricular end diastolic pressure) was established to 5 mmHg and this volume of balloon was consistently maintained throughout overall experimental procedure. As the physiological solution, KHBB solution (composition, nM: 112.0 NaCl, 5.0 KCl, 1.2 $MgSO_4$, 1.0 $KH_2PO_4$, 25.0 $NaHCO_3$, 1.25 $CaCi_2$, 11.5 glu pyruvate) was used while maintaining the temperature at 37° C. and was maintained at pH 7.4 by continuously supplying the gas mixture of 95% $O_2$ and 5% $CO_2$ during the procedure of experiment.

Single and Repeated Administration

In the single administration group, the galenic composition of the present invention was suspended in sterilized distilled water and orally administered at a dosage of 1000 mg/kg or 1500 mg/kg 2 hours before operation. In the 7-days repeated administration group, the galenic composition of the present invention was suspended in sterilized distilled water and orally administered once a day at a dosage of 600 or 900 mg/kg. The control group was given sterilized distilled water via oral route for the same period. First, the extracted heart was stabilized with oxygen-saturated physiological solution for 15 minutes and then allowed to induce ischemia for 30 minutes by blocking the supply of KHBB solution for 30 minutes, and after 30 minutes, to attempt the normal reperfusion while left ventricular developed pressure (LVDP), heart rate (HR), double product (DP), coronary flow (CF) and +dp/dt were measured.

2. Statistical Analysis

All the experimental results were represented in terms of mean±standard deviation (S.E.M.) and its statistical significance was examined using Student's paired t-test. When P value is less than 0.05, it is determined that the data has a statistical significance.

3. Experimental Result

1) Effect of the Single Administration of the Galenic Composition on Ischemia and Reperfusion of Heart In the control group for ischemia and reperfusion, left ventricular developed pressure (LVDP) was significantly reduced from 77.0±2.1 mmHg at the time of stabilization before ischemia to 21.1±3.8 mmHg after ischemia and reperfusion. Meanwhile, in the 1000 mg/kg group for the galenic composition of the present invention, although LVDP was significantly reduced from 73.4±1.8 mmHg at the time of stabilization before ischemia to 47.3±4.0 mmHg after ischemia and reperfusion, a decrease in LVDP due to ischemia and reperfusion was significantly inhibited in comparison to the control group. In the 1500 mg/kg group for the galenic composition, LVDP was significantly reduced from 82.6±0.5 mmHg before ischemia to 4.0±0.5 mmHg after reperfusion even in comparison to the control group. In the control group, heart rate (HR) was 278.3±11.3 beats/min. before ischemia and, however, was significantly reduced to 232.7±13.5 beats/min. after ischemia and reperfusion. However, in the 1000 mg/kg group for the galenic composition of the present invention heart rate after reperfusion was 257.1±21.7 beats/min., which was not greatly different from the heart rate of 279.7±25.1 beats/min. before ischemia. The double product rate (DP), which indirectly represents the heart function, was significantly reduced from 21.4±0.1 to 5.1±1.1 in the control group. The 1000 mg/kg group for the galenic composition of the present invention exhibited a significant decrease in DP from 20.5±1.5 to 12.0±0.2 but inhibited a decrease in DP due to ischemia and reperfusion in comparison to the control group. In the control group, dP/dT, which is the differential value of left ventricular systolic pressure, was significantly reduced from 1004.3±33.0 before ischemia to 267.0±58.9 after ischemia and reperfusion. However, in the 1000 mg/kg group for the galenic composition of the present invention dP/dT after ischemia was significantly reduced from 953.6±29.0 before ischemia to 733.0±22.0, and however, such reduction in dP/dT was significantly inhibited. In the 1500 mg/kg group for the galenic composition, dP/dT was significantly reduced in comparison to the control group. The coronary flow (CF) was significantly reduced from 12.4±11.1 before ischemia to 9.0±1.0 after reperfusion in the control group. However, in the 1000 mg/kg group for the galenic composition of the present invention CFs before ischemia and after reperfusion were 12.0±1.0 and 10.0±1.5, respectively and therefore, have no great difference from each other. In the 1500 mg/kg group for the galenic composition CF after reperfusion did not greatly differ from CF before ischemia. The experimental results are described in the following Table 11.

TABLE 11

Effect of the single administration of the galenic composition on the damage of heart, function due to ischemia and reperfusion

| Parameters | Pre-ischemia | Reperfusion |
|---|---|---|
| LVDP (mmHg) | | |
| Control group | 77.0 ± 2.1 | 21.1 ± 3.8** |
| Galenic composition (mg/kg) | | |
| 1000 | 73.4 ± 1.8 | 47.3 ± 4.0##* |
| 1500 | 82.6 ± 0.5# | 4.0 ± 5##** |

TABLE 11-continued

Effect of the single administration of the galenic composition on the damage of heart, function due to ischemia and reperfusion

| Parameters | Pre-ischemia | Reperfusion |
|---|---|---|
| HR (beats/min.) | | |
| Control group | 278.3 ± 11.3 | 232.7 ± 13.5* |
| Galenic composition (mg/kg) | | |
| 1000 | 279.7 ± 25.1 | 257.1 ± 21.7 |
| 1500 | 238.2 ± 8.5 | 225.8 ± 8.3 |
| DP (LVDPx;HR/1000) | | |
| Control group | 21.4 ± 0.1 | 5.1 ± 1.1** |
| Galenic composition (mg/kg) | | |
| 1000 | 20.5 ± 1.5 | 12.0 ± 0.2##* |
| 1500 | 19.7 ± 1.4 | 0.9 ± 0.1##** |
| ± dP/dTmax (mmHg/sec) | | |
| Control group | 1004.3 ± 33.0 | 267.0 ± 58.9** |
| Galenic composition (mg/kg) | | |
| 1000 | 953.6 ± 29.0 | 733.0 ± 22.0##** |
| 1500 | 1001.6 ± 3.0 | 42.3 ± 6.0##** |
| CF (ml) | | |
| Control group | 12.4 ± 1.1 | 9.0 ± 1.0* |
| Galenic composition (mg/kg) | | |
| 1000 | 12.0 ± 1.0 | 10.0 ± 1.5 |
| 1500 | 15.0 ± 0# | 12.2 ± 1.1 |

Note) *, ** (1)<0.05, p<0.0#) : Significantly different from the pre-ischemia in 95% and 99% confidence interval
ft (p<0.05, p<0.01) : Significantly different from the control group in 95% and 99% confidence interval
LVDP: left ventricular developed pressure
HR : heart rate
DP : double product
CF : coronary flow In the above table, the numerical values were recorded in terms of mean±standard deviation (S.E.N.) and each test group used heart extracted from 6 animals.

2) Effect of the Repeated Administration of the Galenic Composition on Angina Pectors-induced Heart In the control group for ischemia and reperfusion, left ventricular developed pressure (LVDP) was significantly reduced from 77.0±2.1 mmHg before ischemia to 21.1±3.8 mmHg after ischemia and reperfusion. Meanwhile, in the 600 mg/kg group for the galenic composition of the present invention, although LVDP was reduced from 68.9±2.5 mmHg before ischemia to 59.4±3.7 mmHg after ischemia and reperfusion, a decrease in LVDP due to ischemia and reperfusion was significantly inhibited in comparison to the control group. In the 900 mg/kg group for the galenic composition, LVDP was significantly reduced from 74.9±2.6 mmHg before ischemia to 29.1±18.5 mmHg after reperfusion. In the control group, heart rate (HR) was significantly reduced from 278.3±11.3 beats/min. before ischemia to 232.7±13.5 beats/min. after ischemia and reperfusion. In the 600 mg/kg group for the galenic composition of the present invention heart rate after reperfusion was 249.8±24.0 beats/min., which was not greatly different from the heart rate of 295.8±30.6 beats/min. before ischemia. In the 900 mg/kg group for the galenic composition of the present invention heart rate after reperfusion was 233.7±11.3 beats/min., which does also not greatly differ from the heart rate of 270.9±6.0 beats/min. before ischemia. In case of the double product, the control group exhibited a significant reduction from 21.4±0.1 before ischemia to 5.1±1.1 after reperfusion. The 600 mg/kg group for the galenic composition of the present invention exhibited a decrease in DP from 20.3±1.8 to 14.9±2.0 but inhibited a decrease in DP due to ischemia and reperfusion in comparison to the control group. In the 900 mg/kg group for the galenic composition of the present invention DP after reperfusion was reduced from 20.3±0.4 to 6.6±1.7, which does also not greatly differ from the control group. In the control group, dP/dT, which is the differential value of left ventricular systolic pressure, was significantly reduced from 1004.3±33.0 before ischemia to 267.0±58.9 after ischemia and reperfusion. However, in the 600 mg/kg group for the galenic composition of the present invention dP/dT after ischemia was reduced from 977.7±10.1 before ischemia to 951.0±43.2, and however, such reduction in dP/dT was significantly inhibited. In the 900 mg/kg group for the galenic composition, dP/dT was significantly reduced to 415.7±133.0 in comparison to the dP/dT value of 939.9±46.2 before ischemia. The coronary flow (CF) was significantly reduced from 12.4±1.1 before ischemia to 9.0±1.0 after reperfusion in the control group. However, CF values were 16.0±2.3 before ischemia and 13.3±1.6 after reperfusion in the 600 mg/kg group for the galenic composition of the present invention and 13.3±1.6 before ischemia and 10.5±0.9 after reperfusion in the 900 mg/kg group for the galenic composition, and therefore, in both groups CF values after reperfusion did not greatly differ from CF values before ischemia. The experimental results are described in the following Table 12.

TABLE 12

Effect of the 7-dyas repeated administration of the galenic composition on the damage of heart function due to ischemia and reperfusion

| Parameters | Pre-ischemia | Reperfusion |
|---|---|---|
| LVDP (mmHg) | | |
| Control group | 77.0 ± 2.1 | 21.1 ± 3.8** |
| Galenic composition (mg/kg) | | |
| 600 | 68.9 ± 2.5 | 59.4 ± 3.7## |
| 900 | 74.9 ± 2.6 | 29.1 ± 8.5* |
| HR (beats/min.) | | |
| Control group | 278.3 ± 1 1.3 | 232.7 ± 13.5* |
| Galenic composition (mg/kg) | | |
| 600 | 295.8 ± 30.6 | 249.8 ± 24.0 |
| 900 | 270.9 ± 6.0 | 233.7 ± 1 1.3 |
| DP (LVDPx;HR/1000) | | |
| Control group | 21.4 ± 0.1 | 5.1 ± 1.1** |
| Galenic composition (mg/kg) | | |
| 600 | 20.3 ± 1.8 | 14.9 ± 2.0# |
| 900 | 20.3 ± 0.4 | 6.6 ± 1.7* |
| +dP/dTmax (mmHg/sec) | | |
| Control group | 1004.3 ± 33.0 | 267.0 ± 58.9** |
| Galenic composition (mg/kg) | | |
| 600 | 977.7 ± 10. 1 | 951.0 ± 43.2## |
| 900 | 939.9 ± 46.2 | 415.7 ± 133.0* |
| CF (ml) | | |
| Control group | 12.4 ± 1.1 | 9.0 ± 1.0* |
| Galenic composition (mg/kg) | | |
| 600 | 16.0 ± 2.3 | 13.3 ± 1.6 |
| 900 | 13.3 ± 1.6 | 10.5 ± 0.9 |

Note) *, ** (p < 0.05, p < 0.01) : Significantly different from the pre-ischemia in 95% and 99% confidence interval
, ## (p < 0.05, p < 0.01) : Significantly different from the control group in 95% and 99% confidence interval
LVDP : left ventricular developed pressure
HR : heart rate
DP : double product
CF : coronary flow In the above table, the numerical values were recorded in terms of mean±standard deviation (S.E.N.) and each test group used heart extracted from 6 animals.

4. Conclusion

As reviewed above, according to the test for evaluating the effect of the galenic composition of the present invention comprising the mixed extract of medicinal herbs on ischemic and reperfused hearts extracted from rats it could be identified that the single administration of the galenic composition of the present invention at a dosage of 1000 mg/kg exhibited an effect of inhibiting the damage of heart function due to ischemia and reperfusion. Further, in the test for the repeated administeration of the galenic composition of the present invention for 7 days at two kinds of dosages, the 600 dosing group exhibited an effect of preventing and inhibiting the damage of heart function due to ischemia and reperfusion.

As can be seen from the results obtained from the above-mentioned numerous experiments, it could be identified that the galenic composition of the present invention comprising 8 kinds of medicinal herbs, as defined above, is very effective for preventing and treating hyperlipidemia and angina pectoris due to myocardial ischemia, through numerous activities and mechanisms originated from respective medicinal herbs.

While the invention has been described with respect to the above specific embodiments, it should be recognized that various modifications and changes can be made to the invention by those skilled in the art which also fall within the scope of the invention as defined by the appended claims.

What is claimed is:

1. A therapeutic composition for treating hyperlipidemia and angina pectoris, which comprises the following herbal components: *Allium thumbergii*, trichosanthis semen, angelicae gigantis radix, salviae radix, cinnamomi ramulus, curcumae tuber, paeoniae rubrae radix and pinelliae rhizoma contained in a ratio of 1–10:0.5–6:0.5–6:0.5–6:0.1–5:0.1–5:0.1–5:0.1–5, respectively, on the basis of dry weight, whereby the herbal components are extracted with a heated combination of water and rice wine.

2. The therapeutic composition for treating hyperlipidemia and angina pecoris according to claim 1, wherein the *Allium thumbergii*, trichosanthis semen, angelicae gigantis radix, salviae radix, cinnamomi ramulus, curcumae tuber, paeoniae rubrae radix and pinelliae rhizoma are contained in a ratio of 3–6:1–4:1–4:1–4:0.5–3:0.5–3:0.5–3:0.5–3, respectively, on the basis of dry weight.

3. The therapeutic composition for treating hyperlipidemia and angina pectoris according to claim 2, wherein the *Allium thumbergii*, trichosanthis semen, angelicae gigantis radix, salviae radix, cinnamomi ramulus, curcumae tuber, paeoniae rubrae radix and pinelliae rhizoma are contained in a ratio of 1.5:0.8:0.8:0.8:0.6:0.6:0.6:0.6, respectively, on the basis of dry weight.

4. The therapeutic composition for treating hyperlipidemia and angina pectoris according to claim 1, further comprising a white liquor as an adjuvant substance.

5. The therapeutic composition for treating hyperlipidemia and angina pectoris according to claim 4, wherein the white liquor is one or more selected from the group consisting of Kaoliang wine, clear strained rice wine and refined rice wine.

* * * * *